(12) United States Patent
Yahata et al.

(10) Patent No.: US 9,588,050 B2
(45) Date of Patent: Mar. 7, 2017

(54) TOTAL NITROGEN MEASUREMENT APPARATUS

(75) Inventors: Yoshihito Yahata, Kyoto (JP); Yoshizou Ishida, Kyoto (JP); Takao Shimotani, Kyoto (JP); Satoshi Takemura, Kyoto (JP); Takayuki Mamiya, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 18 days.

(21) Appl. No.: 14/378,694

(22) PCT Filed: Feb. 17, 2012

(86) PCT No.: PCT/JP2012/053790
§ 371 (c)(1),
(2), (4) Date: Oct. 29, 2015

(87) PCT Pub. No.: WO2013/121577
PCT Pub. Date: Aug. 22, 2013

(65) Prior Publication Data
US 2016/0054228 A1    Feb. 25, 2016

(51) Int. Cl.
*G01N 21/75* (2006.01)
*G01N 31/00* (2006.01)
(Continued)

(52) U.S. Cl.
CPC .............. *G01N 21/75* (2013.01); *G01N 21/33* (2013.01); *G01N 21/631* (2013.01); *G01N 31/005* (2013.01); *G01N 33/188* (2013.01)

(58) Field of Classification Search
CPC .... G01N 21/75; G01N 31/005; G01N 21/631; G01N 21/33; G01N 33/188;
(Continued)

(56) References Cited

U.S. PATENT DOCUMENTS 5,567,621 A    10/1996 Tahara et al.
5,582,944 A *  12/1996 Yamamura ......... G03G 5/08228
                                                        430/58.1

FOREIGN PATENT DOCUMENTS

CN    2555504 Y    6/2003
CN    1506672 A    6/2004
(Continued)

OTHER PUBLICATIONS

JP200344381, Machine English Translation, No date.*
(Continued)

*Primary Examiner* — Jill Warden
*Assistant Examiner* — Julie Tavares
(74) *Attorney, Agent, or Firm* — Westerman, Hattori, Daniels & Adrian, LLP

(57) ABSTRACT

A total nitrogen measurement apparatus comprising an ultraviolet lamp comprising: a light emission section and a holding section for holding the light emission section, the holding section being formed of a material not including iron; a reaction vessel having a space where the light emission section is to be inserted and a sample water is to be contained around the light emission section for converting nitrogen compounds in the sample water contained in the reaction vessel into nitrate ions by oxidative decomposition using ultraviolet rays from the light emission section; and a measurement section configured to perform absorbance measurement on the sample water including the nitrate ions.

2 Claims, 4 Drawing Sheets

(51) Int. Cl.
*G01N 33/18* (2006.01)
*G01N 21/33* (2006.01)
*G01N 21/63* (2006.01)

(58) Field of Classification Search
CPC ........ G01N 31/00; B01D 53/54; B01D 53/56; B01D 53/565; B01D 53/8625; B01D 53/8631; C02F 1/32
USPC .................................................. 436/106, 107
See application file for complete search history.

(56) References Cited

FOREIGN PATENT DOCUMENTS

| JP | 07-27706 A | 1/1995 |
|---|---|---|
| JP | 07-311155 A | 11/1995 |
| JP | 09-281099 A | 10/1997 |
| JP | 2001-056332 A | 2/2001 |
| JP | 2001-83083 A | 3/2001 |
| JP | 2001-194357 A | 7/2001 |
| JP | 2003-344381 A | 12/2003 |
| JP | 2006-201104 A | 8/2006 |

OTHER PUBLICATIONS

Yan-Zhi et al., "New Method for Eliminating the Iron Ions Interference in the Determination of Nitrate by UV Spectrophotometry", Chinese Journal of Spectroscopy Laboratory, vol. 28, No. 6, pp. 3143-3147, Nov. 2011. (6 pages), cited in Chinese Office Action dated Mar. 10, 2015, with English Abstract.

Office Action dated Mar. 10, 2015, issued in corresponding Chinese application No. 201280069341.3 (8 pages).

JIS handbook 53, Kankyo Sokutei II, Jan. 31, 2003, pp. 534-537.

Takada A et al , "Effects of metal ions in total nitrogen measurement" (ultraviolet absorption spectrophotometry) Zenchisso Sokutei (Shigaisen Kyuko Kodoho) ni Okeru Kinzoku Ion no Eikyo ni Tsuite, Mizushori Gijutsu, Dec. 15, 1999 , vol. 40,No. 12, pp. 577-582.

* cited by examiner

TOTAL NITROGEN MEASUREMENT APPARATUS

TECHNICAL FIELD

The present invention relates to a total nitrogen measurement apparatus including a reaction vessel having a space where a light emission section of an ultraviolet lamp is to be inserted and where a sample is to be contained in a space around the ultraviolet lamp, the total nitrogen measurement apparatus being for measuring the concentration of nitrogen compounds in a sample by decomposing nitrogen compounds by oxidation by holding, in the reaction vessel, a sample water to which a reactive reagent is added to perform oxidative decomposition of nitrogen compounds and radiating ultraviolet rays from the ultraviolet lamp on the sample water, and performing absorbance measurement on the sample water obtained after the nitrogen compounds have been decomposed by oxidation.

BACKGROUND ART

Generally, as a method of measuring total nitrogen in wastewater discharged from factories and the like, "Ultraviolet spectrophotometry" defined in "Testing methods for industrial wastewater discharged from factories" according to Japanese Industrial Standards is used. This is a method of adding alkaline potassium peroxodisulfate, which is an oxidizing agent, to a sample water, decomposing nitrogen compounds into nitrate ions in a high-temperature and high-pressure environment by thermal decomposition, and determining total nitrogen concentration by absorbance measurement at 220 nm. However, a measurement apparatus to be used for this method has to be resistant to pressure and heat, thus requiring special materials and design.

As another method of decomposing nitrogen compounds in a sample water into nitrate ions by oxidation, there is an "ultraviolet oxidative decomposition method". According to this method, total nitrogen concentration is determined by decomposing nitrogen compounds in a sample water to which alkaline potassium peroxodisulfate, which is an oxidizing agent, is added into nitrate ions by oxidation by radiating ultraviolet rays on the sample water under a condition of predetermined temperature and pressure, and measuring the absorbance of the sample water at 220 nm. This method is improved in reducing the pressure and temperature for the sample water, and the temperature necessary for oxidative decomposition of nitrogen oxide by ultraviolet rays is reduced to about 60° C. from conventional 120° C., and also, the pressure may be a normal pressure, and thus, the apparatus is not required to be highly resistant to pressure and heat.

PRIOR ART DOCUMENTS

Patent Documents

Patent Document 1: Japanese Patent Laid-open Publication No. 2003-344381

SUMMARY OF THE INVENTION

Problems to be Solved by the Invention

As an apparatus that uses the ultraviolet oxidative decomposition method, there is an apparatus that adopts a structure according to which, to increase the efficiency of oxidative decomposition of nitrogen compounds, a light emission section of an ultraviolet lamp is inserted inside a reaction vessel of an oxidative decomposition section, and ultraviolet rays are radiated on the nitrogen compounds in a sample water with the light emission section immersed in the sample water (see Patent Document 1). However, a detection signal obtained by performing total nitrogen measurement by an apparatus adopting such a structure sometimes includes a signal which is thought to be caused by the influence of a substance different from the nitrate ions generated by oxidative decomposition of the nitrogen compounds, and the cause of the obtained detection signal is yet to be explained.

Accordingly, the present invention aims to prevent, in measurement of absorbance of a sample water including nitrate ions which have been converted by ultraviolet radiation, interference in total nitrogen measurement by substances other than the nitrate ions.

Solutions to the Problems

The present invention is a total nitrogen measurement apparatus including a reaction vessel having a space where a light emission section of an ultraviolet lamp is to be inserted and where a sample is to be contained in a space around the ultraviolet lamp, the total nitrogen measurement apparatus being for measuring a total nitrogen concentration of a sample water by converting nitrogen compounds into nitrate ions by oxidative decomposition by holding, in the reaction vessel, a sample to which a reactive reagent is added to perform oxidative decomposition of the nitrogen compounds and radiating ultraviolet rays from the ultraviolet lamp on the sample water, and performing absorbance measurement on the sample water including the nitrate ions, wherein a holding section for holding the light emission section of the ultraviolet lamp is formed of a material not including iron.

In the case of performing total nitrogen measurement by measuring the absorbance around 220 nm, measurement is affected by substances having absorption in a wavelength range around 220 nm. Among such substances, an iron ion greatly interferes with total nitrogen measurement, and thus, a structure is adopted according to which a member formed of an iron-based material does not come into contact with a sample water. Nevertheless, a noise presumably caused by a component different from the nitrate ion is included in a detection signal.

The present inventors have found out that the cause of the noise is the ultraviolet lamp which is for radiating ultraviolet rays on the sample water to decompose the nitrogen compounds by oxidation. That is, although the only part of the ultraviolet lamp that comes into contact with a sample water is a light emission section formed of a material not including iron-based material, such as a quartz glass tube, an external cylinder portion of a holding section for holding the base portion of the light emission section is made of iron-based material. The holding section does not come into direct contact with a sample water, but it has been found that a sample water to which sulfuric acid or the like is added may evaporate and stick to a surface of the holding section, and that iron ions may dissolve into the sample water from that portion.

Effects of the Invention

Based on the above understanding, according to the present invention, the holding section for holding the light emission section of the ultraviolet lamp is formed by a material not including iron. Accordingly, iron ions are not generated even when a reagent that reacts with iron is evaporated and is stuck to the surface of the holding section of the ultraviolet lamp, and interference in the total nitrogen measurement by iron ions may be prevented.

DESCRIPTION OF REFERENCE SIGNS

Figure 1:
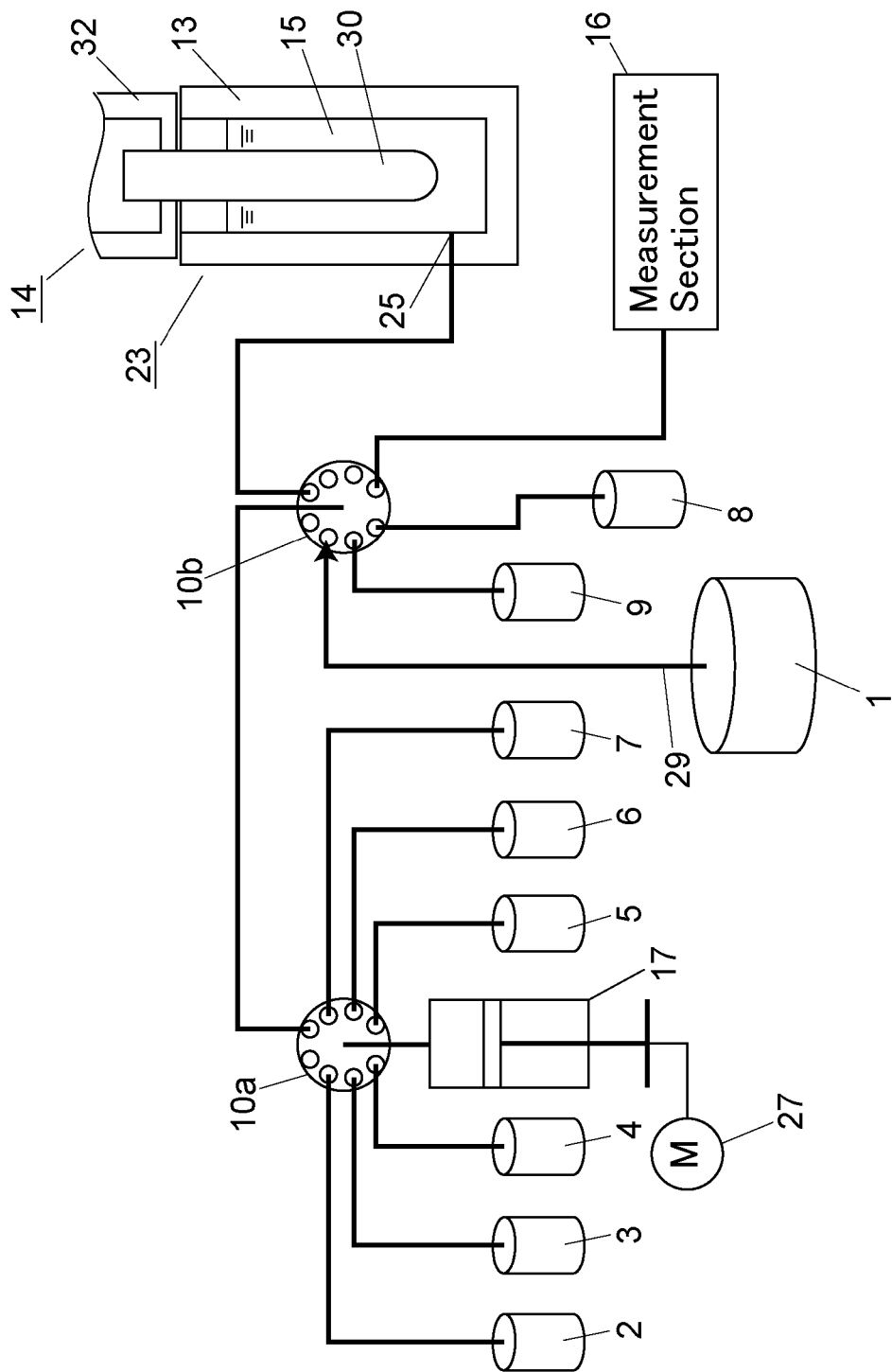
FIG. 1 is a path diagram schematically showing an embodiment of a total nitrogen measurement apparatus.

1: Sample preparation tank
2 to 9: Reagent containers
10a, 10b: Multiport valve
13: Reaction vessel
14: Ultraviolet lamp
15: Sample water
16: Measurement section
23: Oxidation reactor
30: Light emission section
32: Holding section
34: Lead wire
36: Filler Embodiments of the Invention According to a preferred embodiment of a total nitrogen measurement apparatus of the present invention, a holding section for holding a light emission section of an ultraviolet lamp is formed of resin not including a nitrogen component.

In the following, an embodiment of the total nitrogen measurement apparatus will be described with reference to FIG. 1. The total nitrogen measurement apparatus includes two multiport valves 10a and 10b. A sample preparation tank 1 where a sample is prepared and stored is connected to one port of one multiport valve 10b by a tube 29. In addition to a container 8 containing span solution and a container 9 containing pure water, a sample inlet/outlet 25 of an oxidation reactor 23, a measurement section 16 and the like are connected to other ports of the multiport valve 10b. Also, the common port of the multiport valve 10b is connected to one port of the other multiport valve 10a.

Containers 2 to 7 containing various solutions are connected to the ports of the multiport valve 10a by pipes. In the present embodiment, potassium peroxodisulfate solution is contained in the container 2, aqueous sodium hydroxide is contained in the container 3, hydrochloric acid solution is contained in the container 4, ascorbic acid solution is contained in the container 5, molybdic acid solution is contained in the container 6, and sulfuric acid solution is contained in the container 7.

A syringe pump 17 is connected to the common port of the multiport valve 10a. The syringe pump 17 is driven by a motor 27, and performs suction and discharge of various liquids.

The oxidation reactor 23 decomposes nitrogen compounds in a sample into nitrate ions by oxidation. The oxidation reactor 23 has a light emission section 30 of an ultraviolet lamp 14, such as a low pressure mercury lamp, inserted inside a reaction vessel 13, and is configured to contain a sample water 15 around the ultraviolet lamp 14. Although not shown, the reaction vessel 13 is provided with a heater, and may heat a contained sample to a predetermined temperature. The temperature at which the sample water is heated is preferably 100° C. or lower.

The measurement section 16 measures the absorbance of the sample water after oxidation reaction, and although detailed illustration is omitted, the measurement section 16 is provided with a sample cell, a light source for radiating light of, for example, 220 nm on the sample cell, a sensor for detecting light transmitted through the sample cell, and the like.

Figure 3:
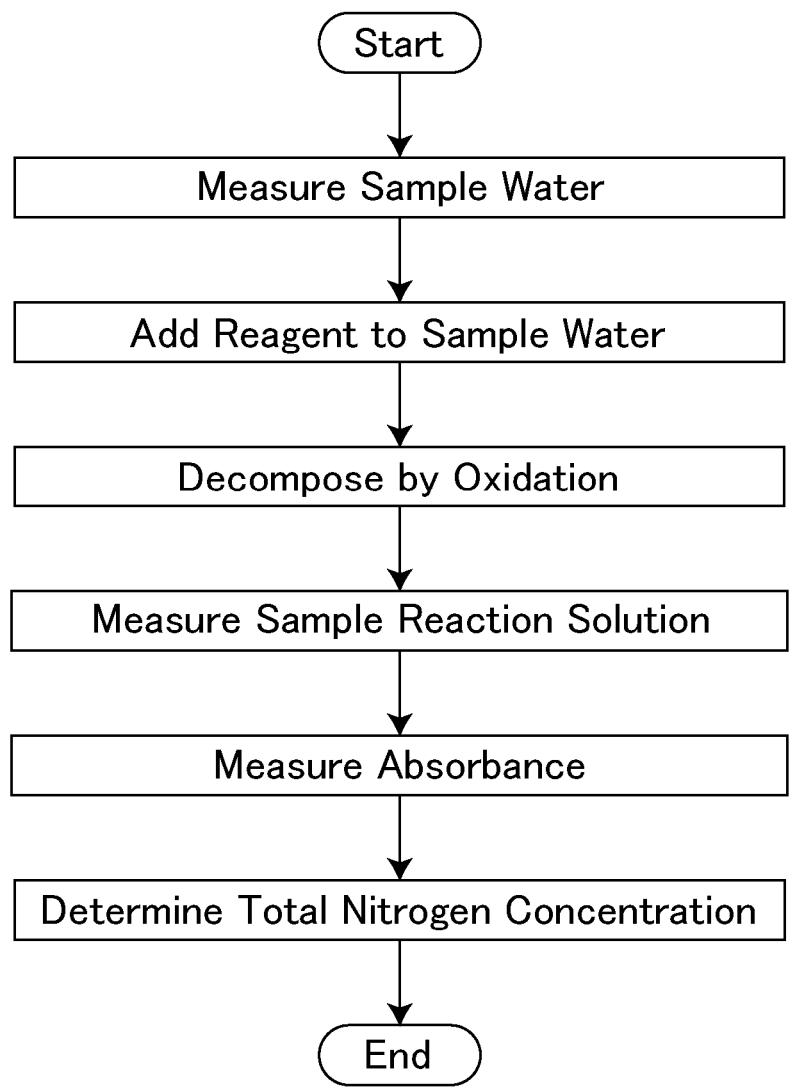
FIG. 3 is a flow chart showing a total nitrogen measurement operation of the total nitrogen measurement apparatus according to the embodiment.

Next, a measurement operation of the total nitrogen measurement apparatus will be described with reference to the flow chart of FIG. 3.

The syringe pump 17 measures a sample water from the sample preparation tank 1. The pure water 9 is suctioned by the syringe pump 17 as necessary, and the sample water is diluted to be, for example, 2 mgN/L or less.

A solution obtained by adding the potassium peroxodisulfate solution 2 and the sodium hydroxide solution 3 to the sample water is introduced into the reaction vessel 15 of the oxidation reactor 23 heated to about 60 to 80° C. At the oxidation reactor 23, ultraviolet rays are radiated by the ultraviolet lamp 14 for about 20 minutes, and nitrogen compounds are decomposed by oxidation into nitrate ions. Subsequently, a predetermined amount of solution after the oxidation reaction is measured by the syringe pump 17, and is transmitted to the measurement section 16 after addition of the hydrochloric acid solution 4. Then, the absorbance at 220 nm is measured at the measurement section 16, and the total nitrogen concentration is obtained.

Figure 2:
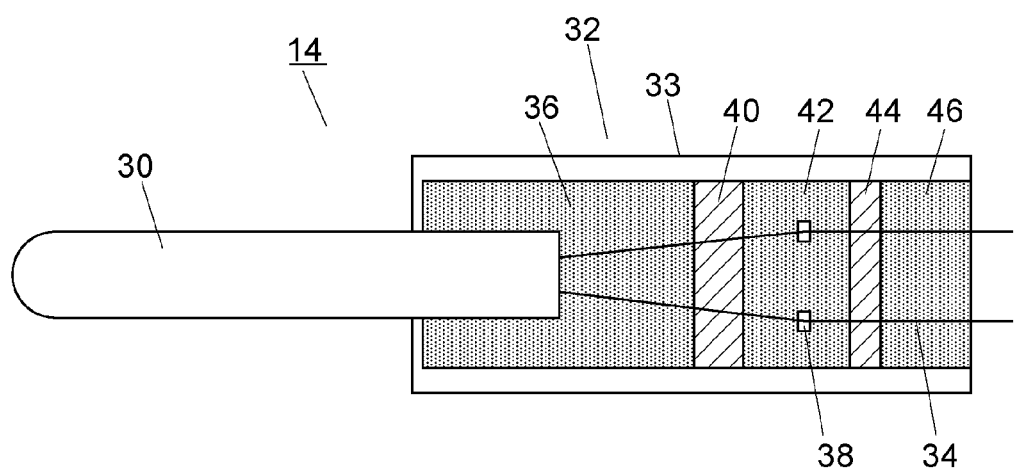
FIG. 2 is a cross-sectional diagram showing an example of a structure of an ultraviolet lamp according to the embodiment.

Here, the ultraviolet lamp 14 used by the oxidation reactor 23 will be described with reference to FIG. 2.

The ultraviolet lamp 14 includes a light emission section 30 at its tip, and a base portion of the light emission section 30 is held by a holding section 32. The holding section 32 includes, at a tip end of an external cylinder portion 33, a hole for passing through the light emission section 30, and a layer 36 formed by solidified filler filled inside the external cylinder portion 33 holds the base portion of the light emission section 30. The external cylinder portion 33 of the holding section 32 is formed of a material other than iron, such as ceramics, alumina, quartz glass, Pyrex (registered trademark) glass, fluoro rubber (for example, Viton (registered trademark)), or tetrafluoroethylene. When these materials are used for the external cylinder portion 33, the filler for forming the layer 36 inside the external cylinder portion 33 may be made of low-thermal-expansion silicone resin, epoxy resin, cement, or the like. In the present embodiment, the layer 36 of the filler is formed of silicone resin, and an epoxy resin layer 40, a silicone resin layer 42, an epoxy resin layer 44, and a silicone resin layer 46 are formed, in this order from the silicone resin layer 36, on the side of the silicone resin layer 36 opposite the light emission section 30. Two lead wires 34 extending from the base portion of the light emission section 30 are drawn outside the holding section 32 by caulking clamps 38.

At the oxidation reactor 23, only the light emission section 30 of the ultraviolet lamp 14 is inserted inside the reaction vessel 13, and the sample water is contained around this light emission section 30. Potassium peroxodisulfate and sodium hydroxide are added to the sample water to be contained, and these liquids may evaporate and stick to the external cylinder portion of the holding section 32 of the ultraviolet lamp 14, but since the external cylinder portion of the holding section 32 is made of a material other than iron, iron ions that have absorption with respect to light at 220 nm are not generated, and measurement of ultraviolet absorbance is not affected.

Figure 4:
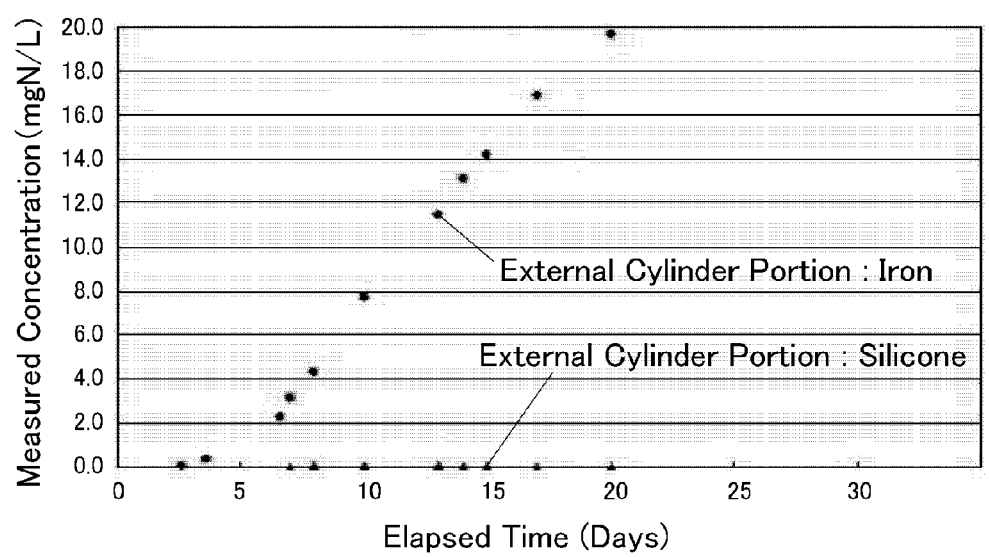
FIG. 4 is measurement data obtained by performing total nitrogen measurement for the same sample for cases where a holding section whose external cylinder portion is made of iron is used in an ultraviolet lamp of an oxidation reactor and where a holding section whose external cylinder portion is made of silicone resin is used in an ultraviolet lamp of an oxidation reactor.

FIG. 4 is measurement data obtained by performing total nitrogen measurement for the same sample for cases where the holding section whose external cylinder portion is made of iron is used in the ultraviolet lamp of the oxidation reactor and where the holding section whose external cylinder portion is made of silicone resin is used in the ultraviolet lamp of the oxidation reactor. As indicated by this data, in the case where the external cylinder portion of the holding section of the ultraviolet lamp is made of iron, the nitrogen concentration that is measured is increased with lapse of time. On the other hand, in the case where the external cylinder portion of the holding section of the ultraviolet lamp is made of silicone resin, the nitrogen concentration that is measured is not changed over time. The reason thereof is assumed to be the dissolution of iron into a reaction solution in the oxidation reactor under an acidic condition by sulfuric acid, the iron which has dissolved into the reaction solution affecting the measurement value of the nitrogen concentration.

Additionally, the total nitrogen measurement apparatus of the present embodiment is also capable of decomposing phosphorous compounds into phosphate ions by adding sulfuric acid to a sample water including phosphorous compounds, introducing the sample water into the oxidative decomposition section 23, and radiating ultraviolet rays at a temperature of 100° C. or lower, and then, of measuring phosphorus concentration by a molybdenum blue method.

What is claimed is:

1. A total nitrogen measurement apparatus comprising:
   an ultraviolet lamp comprising a light emission section and a holding section for holding a base portion of the light emission section;
   a reaction vessel having a space where the light emission section is to be inserted and a sample water is to be contained around the light emission section for converting nitrogen compounds in the sample water contained in the reaction vessel into nitrate ions by oxidative decomposition using ultraviolet rays from the light emission section; and
   a measurement section configured to perform absorbance measurement on the sample water including the nitrate ions,
   wherein the holding section is arranged at a position which is out of the space of the reaction vessel and is not immersed in the sample water, and the holding section is formed of a material not including iron.

2. The total nitrogen measurement apparatus according to claim 1, wherein the holding section is formed of resin not including a nitrogen component.

* * * * *